United States Patent
Chang et al.

(10) Patent No.: US 7,552,635 B2
(45) Date of Patent: Jun. 30, 2009

(54) HUMIDITY SENSOR CAPABLE OF SELF-REGULATING TEMPERATURE COMPENSATION AND MANUFACTURING METHOD THEREOF

(75) Inventors: Chin-Hsiung Chang, Taichung (TW); Yu-Kai Chen, Chiai (TW)

(73) Assignee: Fego Precision Industrial Co., Ltd., Taichung (TW)

( * ) Notice: Subject to any disclaimer, the term of this patent is extended or adjusted under 35 U.S.C. 154(b) by 31 days.

(21) Appl. No.: 11/767,005

(22) Filed: Jun. 22, 2007

(65) Prior Publication Data

US 2007/0295084 A1 Dec. 27, 2007

(30) Foreign Application Priority Data

Jun. 23, 2006 (TW) .............................. 95122847 A

(51) Int. Cl.
*G01N 27/12* (2006.01)
(52) U.S. Cl. ................................... 73/335.05
(58) Field of Classification Search ............. 73/335.02, 73/335.05, 335.06, 23.21, 29.01, 29.05; 29/595
See application file for complete search history.

(56) References Cited

U.S. PATENT DOCUMENTS

| | | | | |
|---|---|---|---|---|
| 3,703,696 A * | 11/1972 | Browall et al. | ................. | 338/35 |
| 3,873,927 A | 3/1975 | Overall | ......................... | 307/650 |
| 4,419,889 A * | 12/1983 | Muto et al. | .............. | 73/335.02 |
| 4,541,904 A * | 9/1985 | Luder et al. | ................... | 205/106 |
| 4,562,725 A * | 1/1986 | Oka et al. | .................. | 73/29.05 |
| 4,571,543 A | 2/1986 | Raymond et al. | ........... | 324/425 |
| 4,642,601 A * | 2/1987 | Sugawara et al. | ............. | 338/35 |
| 4,649,364 A | 3/1987 | Tanahashi et al. | ............. | 338/14 |
| 4,649,736 A * | 3/1987 | Austin | ....................... | 73/25.05 |
| 4,876,890 A * | 10/1989 | Mercer et al. | ............ | 73/335.03 |
| 4,900,405 A | 2/1990 | Otagawa et al. | ............. | 205/781 |
| 4,928,513 A * | 5/1990 | Sugihara et al. | ............ | 73/25.03 |
| 5,001,453 A * | 3/1991 | Ikejiri et al. | ................... | 338/35 |
| 5,033,284 A | 7/1991 | Belt et al. | ..................... | 73/1.06 |
| 5,136,274 A * | 8/1992 | Shimomura et al. | ........... | 338/35 |
| 6,247,349 B1 * | 6/2001 | Lee et al. | ................... | 73/29.05 |
| 6,342,295 B1 * | 1/2002 | Kobayashi | .................. | 428/323 |
| 6,568,265 B2 * | 5/2003 | Shibue et al. | ............. | 73/335.05 |
| 6,812,821 B2 * | 11/2004 | Fujita et al. | ................... | 338/34 |
| 7,032,448 B2 * | 4/2006 | Hamamoto | .............. | 73/335.04 |
| 7,222,531 B2 * | 5/2007 | Isogai et al. | ............. | 73/335.04 |
| 2002/0071999 A1 * | 6/2002 | Allen et al. | ................... | 430/30 |
| 2004/0194546 A1 * | 10/2004 | Kanehori | ................ | 73/335.04 |

* cited by examiner

*Primary Examiner*—John Fitzgerald
(74) *Attorney, Agent, or Firm*—Rosenberg, Klein & Lee

(57) ABSTRACT

A humidity sensor capable of self-regulating temperature compensation and a manufacturing method thereof overcomes the inaccuracy caused by the resistor value of a conventional humidity-sensitive element changing depending due to changes in the temperature. The present invention proposes disposing two different humidity-sensitive elements in a humidity-sensitive substrate, wherein one humidity-sensitive element includes a saturated salt solution. The humidity-sensitive substrate has two different humidity-sensitive elements for achieving a self-regulating temperature compensation feature. The present invention of the humidity-sensitive element having the saturated salt solution can maintain the amount of humidity in the air regardless of the temperature.

11 Claims, 3 Drawing Sheets

HUMIDITY SENSOR CAPABLE OF SELF-REGULATING TEMPERATURE COMPENSATION AND MANUFACTURING METHOD THEREOF

BACKGROUND OF THE INVENTION

1. Field of the Invention

This invention relates to a humidity sensor and manufacturing method thereof and, more particularly, to a humidity sensor capable of self-regulating temperature compensation and a manufacturing method thereof.

2. Description of the Prior Art

Many kinds of humidity sensors, including those with humidity sensitive ceramic elements, porous oxide humidity sensitive elements, MOS-type semiconductor elements and lithium chloride humidity sensitive elements have been proposed in the past. Among polymer humidity sensitive element field, a resistance type polymer humidity sensitive element is widely used as an electronic metering device, a humidifying/dehumidifying device, and a meteorological measurement device because resistance type polymer humidity sensitive elements have the characteristics of high precision, high stability and fast response speed.

Humidity is very difficult to accurately measure. A psychrometer humidity sensor or a hair hygrometer is unnecessary to modern technology. In the prior art, the output of a capacitive humidity sensor is independent of temperature variations. In contrast, a resistance type humidity sensor is dependent upon temperature and often produces large variations and errors in humidity measurement as a result. However, compared with the resistance type humidity sensor, the capacitive humidity sensor is expensive and the cost of the resulting circuit is high.

A humidity-sensitive element is a simple humidity sensor. The humidity-sensitive element employs a resistor and two kinds of capacitors. The humidity-sensitive element uses a film produced by a humidity-sensitive material to cover a substrate. The humidity-sensitive element uses a resistance rate and a resistance value variation to measure humidity when humid air contacts the film. There are many kinds of humidity-sensitive resistors, for example, a metal oxide humidity-sensitive resistor, a silicon humidity-sensitive resistor, and a ceramic humidity-sensitive resistor. The advantage of the humidity-sensitive resistor is that it is highly sensitive, however, it suffers the disadvantages of bad linearity and cannot be replaced once it is broken.

The linearity and clean air requirements of the humidity-sensitive element are very poor. The humidity-sensitive element is easily dirtied and the precision of its measurement functions thereby affected. Furthermore, the stability and the resistance curve are dependant upon temperature when exposed to external environments for a long time.

SUMMARY OF THE INVENTION

To solve the above problems it is an object of the present invention to provide a humidity sensor capable of self-regulating temperature compensation and a manufacturing method thereof.

The present invention proposes a humidity sensor capable of self-regulating temperature compensation which can be applied to a humidity-sensitive device, the humidity sensor comprising: a humidity-sensitive substrate forming a first conductive electrode and a second conductive electrode; a first humidity-sensitive element disposed on the humidity-sensitive substrate, the first humidity-sensitive element having at least one pin which connects to the first conductive electrode; a second humidity-sensitive element disposed on the humidity-sensitive substrate, the second humidity-sensitive element having at least one pin which connects to the second conductive electrode, wherein a sealed area is formed by disposing a humidity-sensitive material thereon.

The present invention proposes a method for manufacturing a humidity sensor capable of self-regulating temperature compensation, comprising: providing a humidity-sensitive substrate; disposing a first humidity sensor element and a second humidity-sensitive element on the humidity-sensitive substrate, the first humidity-sensitive element and the second humidity-sensitive element having at least one pin each; forming a first conductive electrode and a second conductive electrode on the humidity-sensitive substrate, the first conductive electrode connecting to the pins of the first humidity-sensitive element and the second conductive electrode connecting to the pin of the second humidity-sensitive element; and forming a sealed area by disposing a humidity-sensitive material on the second humidity-sensitive element.

The present invention uses two humidity-sensitive elements to self-regulate temperature compensation. The second humidity-sensitive element employs a saturated salt solution having lower saturated water vapor pressure to form the sealed area. The two humidity-sensitive elements are close together and small in size such that the two humidity-sensitive elements are affected by the same temperature simultaneously. The temperature effect is removed from the humidity-sensitive sensor by using an adequate circuit or program. The two humidity-sensitive elements have similar characteristics when the two humidity-sensitive elements are produced simultaneously. The present invention uses the second humidity-sensitive element as a reference for temperature compensation of the resistance value measured by the first humidity-sensitive element, and utilizes the above-mentioned circuit or program to correct the humidity-sensing error when producing the humidity-sensitive element.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF THE INVENTION

Figure 1:
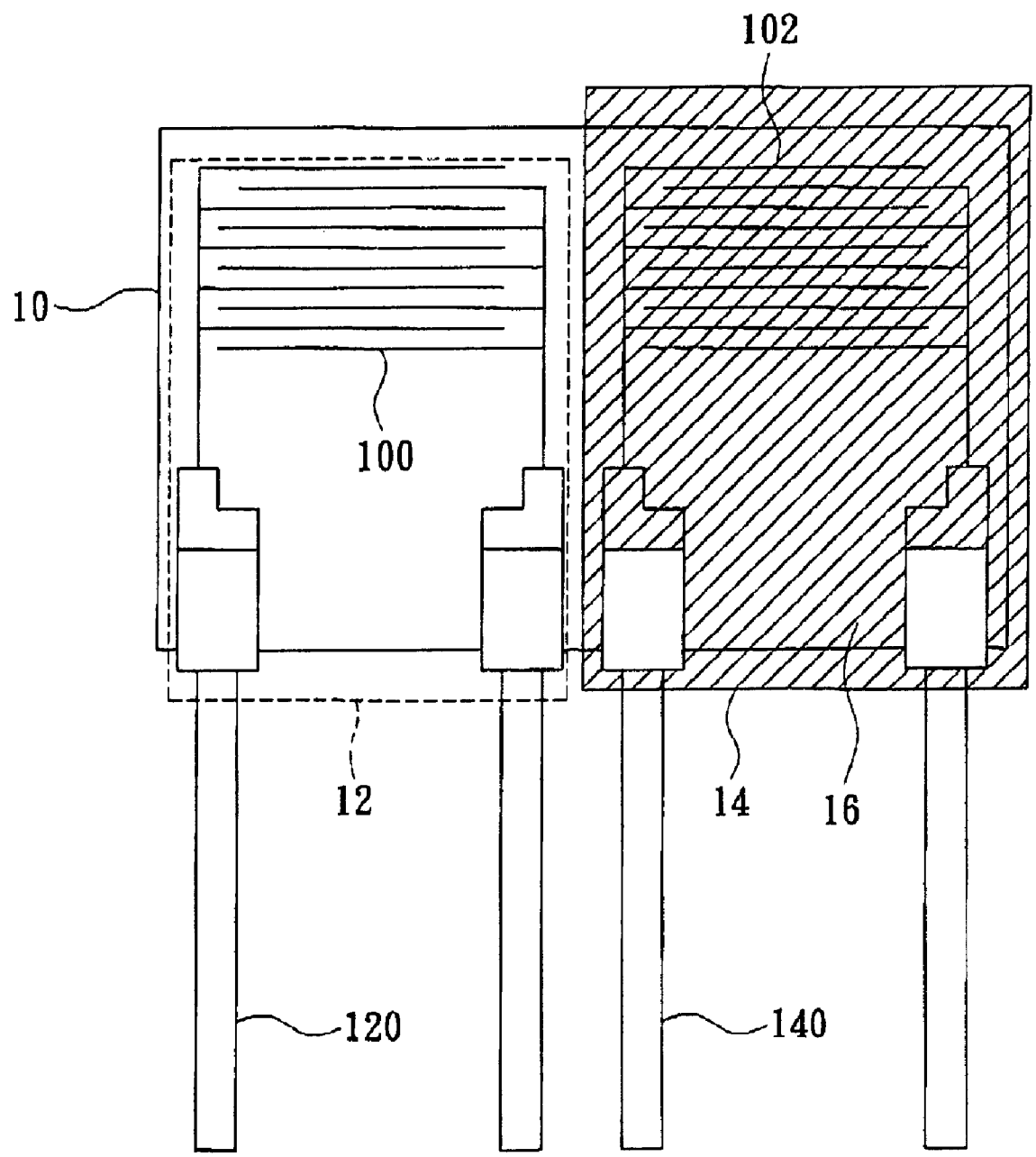
FIG. 1 is a diagram of a humidity sensor capable of self-regulating temperature compensation accordance with the present invention.

Please refer to FIG. 1 which is a diagram of a humidity sensor capable of self-regulating temperature compensation in accordance with the present invention. The humidity sensor comprises a humidity-sensitive substrate 10, a first humidity-sensitive element 12; and a second humidity-sensitive element 14.

The humidity-sensitive substrate 10 may be an SiO2 substrate or a glass substrate. The humidity-sensitive substrate 10 has a first conductive electrode 100 and a second conductive electrode 102 formed thereon. The first humidity-sensitive element 12 is disposed on the humidity-sensitive substrate 10, and has at least one pin 120 that connects to the first conductive electrode 100. The first conductive electrode 100 may be a comb-like metal electrode. The second humidity-sensitive element 14 is disposed on the humidity-sensitive substrate 10, and has at least one pin 140 that connects to the second conductive electrode 102, with a sealed area formed by disposing a humidity-sensitive material 16 thereon. The second conductive electrode 102 may be a comb-like metal electrode. The humidity-sensitive material may be a saturated salt solution, such that the resistance of the sealed area is set according to the saturation level of the saturated salt solution.

Figure 2:
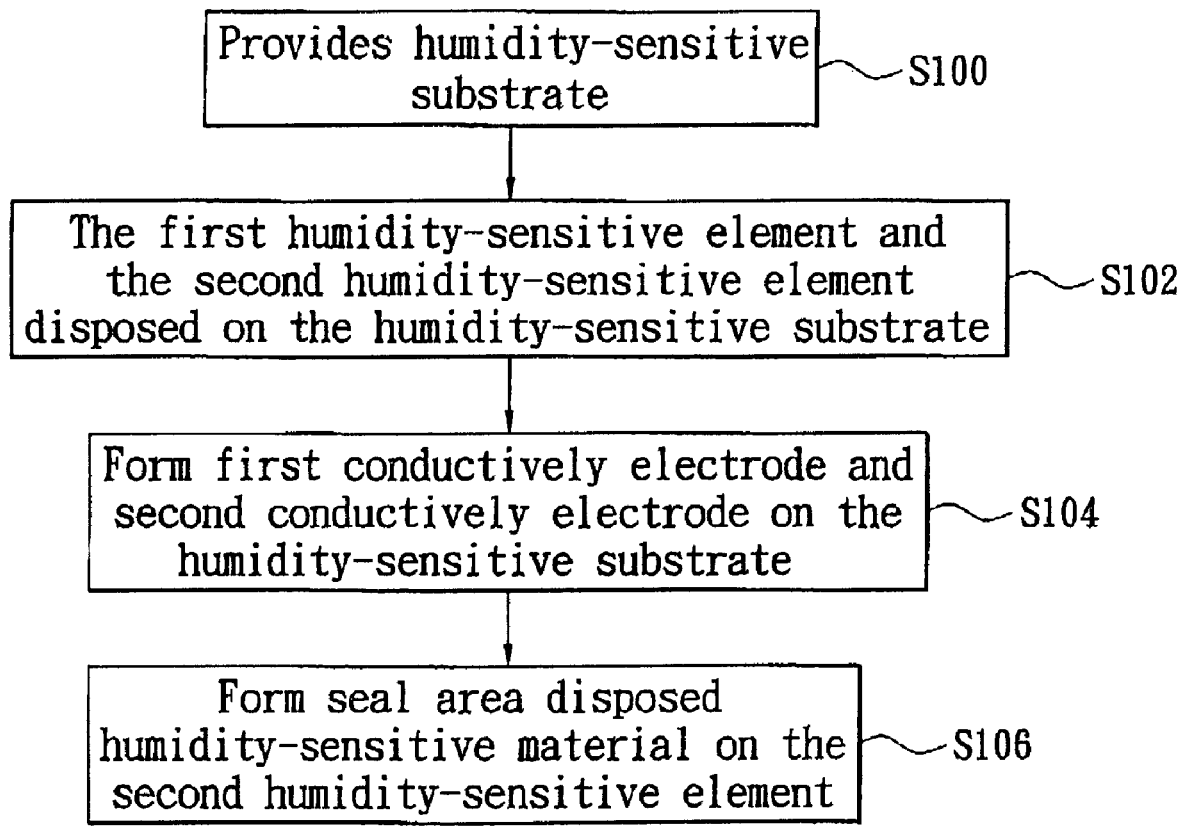
FIG. 2 is a flow chart of a method for manufacturing a humidity sensor capable of self-regulating temperature compensation in accordance with the present invention.

Please refer to FIG. 1 and FIG. 2. FIG. 2 shows a flow chart of a method for manufacturing a humidity sensor capable of self-regulating temperature compensation in accordance with the present invention. The method comprises providing a humidity-sensitive substrate 10 (S100). The humidity-sensitive substrate 10 may be an SiO2 substrate or a glass substrate. The first humidity-sensitive element 12 and the second humidity-sensitive element 14 are disposed on the humidity-sensitive substrate 10. The first humidity-sensitive element 12, and the second humidity-sensitive element 14 have more than one pin 120, 140 (S102).

Next, a first conductive electrode 100 and a second conductive electrode 102 are formed on the humidity-sensitive substrate 10. The first conductive electrode 100 connects to the pins 120 of the first humidity-sensitive element 12, and the second conductive electrode 102 connects to the pins 140 of the second humidity-sensitive element 14 (S104). The first conductive electrode 100 and the second conductive electrode 102 are comb-like metal electrodes. Then, a sealed area is formed with a humidity-sensitive material 16 disposed on the second humidity-sensitive element 14 (S106). The humidity-sensitive material 16 may be a saturated salt solution that includes magnesium oxide, potassium carbonate, magnesium nitrate, sodium chloride, or potassium sulfate. The resistance value of the sealed area is set according to the saturation of the saturated salt solution.

The saturated salt solution has a fixed value so as to provide a reference to the relative humidity of the first humidity sensitive element. But the resistance value of the second humidity element's humidity-sensitive resistor also depends on the same temperature effects encountered by the first humidity-sensitive element. For solving the problem, the present invention utilizes the saturated salt solution disposed on the second humidity-sensitive element to form the sealed area with set resistance reference. Therefore, the second humidity-sensitive element becomes an accurate humidity-controlling element for the first humidity-sensitive element which obtains a humidity value from an outside environment. The humidity sensor of the present invention then obtains an actual humidity by comparison between the humidity value of the first humidity-sensitive element and the original humidity value of the second humidity-sensitive element. The humidity sensor of the present invention thus provides an inherent temperature correcting function because the effects of atmospheric pressure and temperature factors on the elements of the humidity sensor are canceled out. The humidity sensor of the present invention thereby solves the problems of inaccuracy and the instability of the humidity-sensitive element in the prior art.

The humidity sensor of the present invention utilizes two humidity-sensitive elements in order to be self-regulating. The two humidity-sensitive elements are close together and small in size such that the two humidity-sensitive elements experience the same temperature. The resistance value of the first humidity-sensitive element can be changed depending on the sensing of the humidity. The humidity of the second humidity-sensitive element is fixed according to the saturation of the saturated salt solution. Since the two humidity-sensitive elements are subject to the same temperature, the humidity sensor of the present invention can use an accuracy circuit or program to negate the effects of different temperatures thereon.

Figure 3:
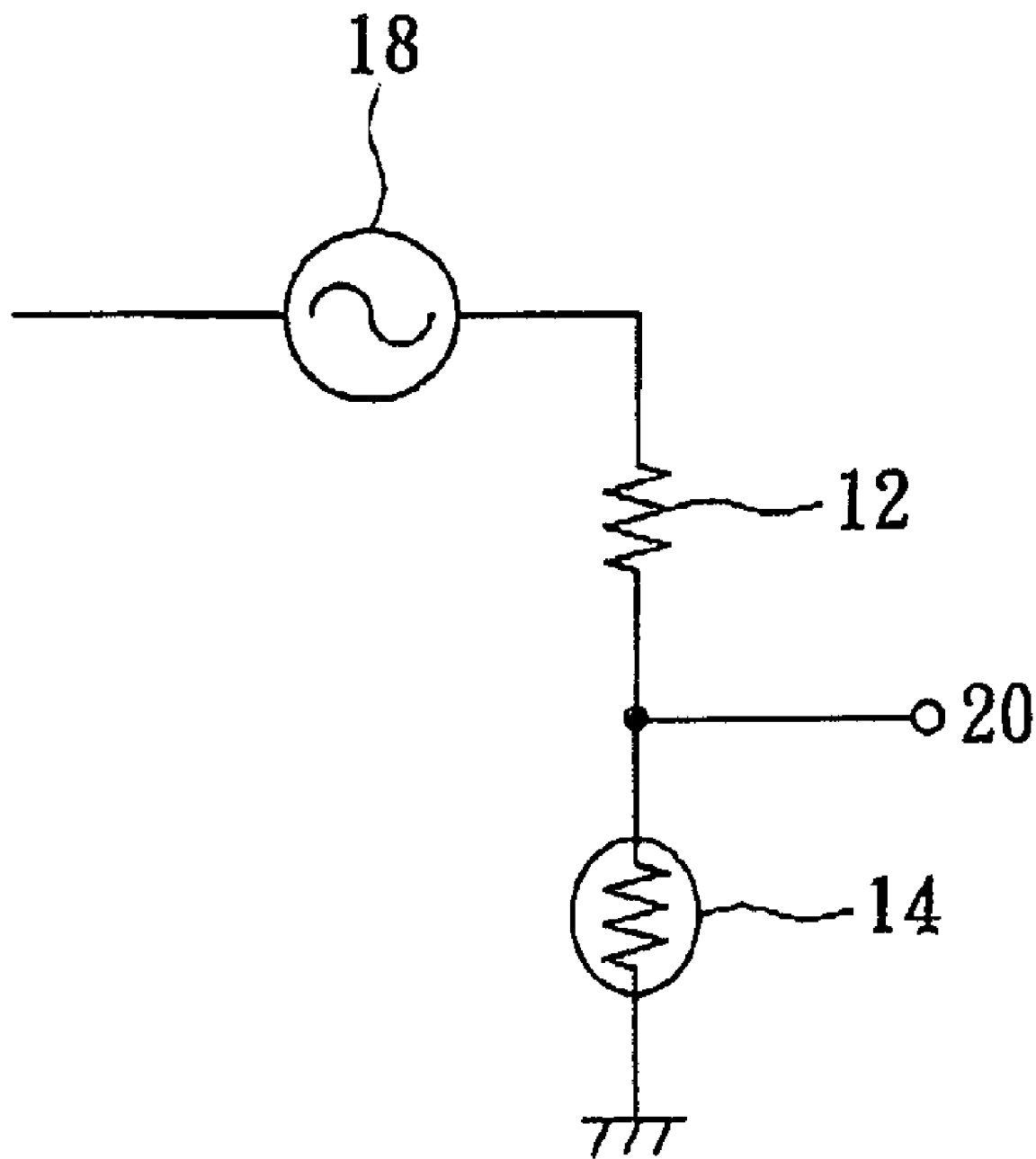
FIG. 3 is simple circuit diagram accordance with the present invention.

Please refer to FIG. 3, which is a simple circuit diagram in accordance with the present invention. The circuit comprises a current source 18, the first humidity-sensitive element 12, and the second humidity-sensitive element 14. The resistance value is changed by a relation ratio that depends on measuring the difference in humidity between the first humidity-sensitive element 12 and the second humidity-sensitive element 14. The present invention overcomes the problems experienced in the prior art. The present invention negates the effects of different temperatures thereby making the temperature to humidity sensor formula more accurate. Therefore, the humidity sensor of the present invention is accurate regardless of the temperature, and achieves the object of temperature compensation.

Furthermore, the two humidity-sensitive elements of the humidity sensor share similar characteristics because the two humidity-sensitive elements are produced simultaneously. The present invention uses the second humidity-sensitive element to provide a temperature compensation reference for measuring the resistance value of the first humidity-sensitive element, and utilizes the above-mentioned circuit or program to correct the humidity-sensitive error in producing the humidity-sensitive element.

However, in the description mentioned above, only the preferred embodiments according to present invention are provided without limitation on the appended claims. Those skilled in the art will recognize equivalent changes and modifications as falling within the scope and spirit of the present invention as set forth in the appended claims.

What is claimed is:

1. A humidity sensor capable of self-regulating temperature compensation for applying on a humidity-sensitive device, the humidity sensor comprising:
   a humidity-sensitive substrate having a first conductive electrode and a second conductive electrode formed thereon;
   a first humidity-sensitive element disposed on the humidity-sensitive substrate, the first humidity-sensitive element including at least one pin connected to the first conductive electrode; and
   a second humidity-sensitive element disposed on the humidity-sensitive substrate, the second humidity-sensitive element including at least one pin connected to the second conductive electrode, the second humidity-sensitive element defining a sealed area having a humidity-sensitive material, the second humidity-sensitive element providing a temperature-responsive reference for a humidity level sensed by the first humidity-sensitive element.

2. The humidity sensor according to claim 1, wherein the humidity-sensitive substrate is an SiO2 substrate or a glass substrate.

3. The humidity sensor according to claim 1, wherein the first conductive electrode and the second conductive electrode are comb-like metal electrodes.

4. The humidity sensor according to claim 1, wherein the humidity-sensitive material is a saturated salt solution.

5. The humidity sensor according to claim 4, wherein a resistance value of the sealed area is set in accordance with a saturation level of the saturated salt solution.

6. A method for manufacturing a humidity sensor capable of self-regulating temperature compensation, comprising:

providing a humidity-sensitive substrate;

disposing a first humidity sensor element and a second humidity-sensitive element on the humidity-sensitive substrate, the first humidity-sensitive element and the second humidity-sensitive element each having at least one pin;

forming a first conductive electrode and a second conductive electrode on the humidity-sensitive substrate, the first conductive electrode connecting to the pins of the first humidity-sensitive element and the second conductive electrode connecting to the pins of the second humidity-sensitive element; and forming a sealed area including a humidity-sensitive material on the second humidity-sensitive element, the second humidity-sensitive element providing a temperature-responsive reference for a humidity level sensed by the first humidity-sensitive element.

7. The method according to claim 6, wherein the humidity-sensitive substrate is an SiO2 substrate or a glass substrate.

8. The method according to claim 6, wherein the first conductive electrode and the second conductive electrode are comb-like metal electrodes.

9. The method according to claim 6, wherein the humidity-sensitive material is a saturated salt solution.

10. The method according to claim 9, wherein the saturated salt solution is magnesium oxide, potassium carbonate, magnesium nitrate, sodium chloride, or potassium sulfate.

11. The method according to claim 9, wherein a resistance value of the sealed area is set in accordance with a saturation level of the saturated salt solution.

* * * * *